United States Patent [19]

Ihara et al.

[11] 4,160,387

[45] Jul. 10, 1979

[54] METHOD AND APPARATUS FOR DETECTING INTERNAL CAVITIES IN CASTING BARS

[75] Inventors: Susumu Ihara; Hiroyuki Yoshimoto; Katsumi Mizuuchi, all of Osaka; Hideo Nishiumi; Takanobu Suzuki, both of Kawasaki, all of Japan

[73] Assignee: Sumitomo Electric Industries, Ltd., Osaka, Japan

[21] Appl. No.: 864,910

[22] Filed: Dec. 27, 1977

[30] Foreign Application Priority Data

Dec. 28, 1976 [JP] Japan .................. 51-159718
Nov. 16, 1977 [JP] Japan .................. 52-138210

[51] Int. Cl.² .......................................... G01N 29/04
[52] U.S. Cl. ............................................... 73/639
[58] Field of Search .............. 73/599, 600, 618, 622, 73/639, 642, 644

[56] References Cited

U.S. PATENT DOCUMENTS

| | | | |
|---|---|---|---|
| 2,912,853 | 11/1959 | Hanyz | 73/642 X |
| 3,550,438 | 12/1970 | Kapluszak | 73/642 |
| 3,625,051 | 12/1971 | Uozumi | 73/639 |

FOREIGN PATENT DOCUMENTS

1294404 10/1972 United Kingdom .................. 73/639

Primary Examiner—Stephen A. Kreitman
Attorney, Agent, or Firm—Sughrue, Rothwell, Mion, Zinn and Macpeak

[57] ABSTRACT

A method and an apparatus for detecting the internal cavities in a continuous casting bar in which two opposite surfaces of a casting bar delivered from a continuous casting machine are held between a pair of rollers each having a hollow portion and are pressurized at a predetermined pressure thereby, and an amount of transmission of an ultrasonic wave having a predetermined frequency passing through the casting bar is detected by means of an ultrasonic wave device for transmission and an ultrasonic wave device for reception which are provided respectively in the hollow portions of the rollers to allow the ultrasonic wave to pass through the casting bar running through the rollers, thereby to detect the internal cavities in the casting bar.

4 Claims, 11 Drawing Figures

METHOD AND APPARATUS FOR DETECTING INTERNAL CAVITIES IN CASTING BARS

BACKGROUND OF THE INVENTION

This invention relates to a method of detecting, by utilizing an ultrasonic wave, internal cavities which may be caused in a continuous casting bar of copper or aluminum, for instance, during the continuous casting and rolling process, and an apparatus for practicing the method.

The internal cavities in a casting bar may cause thermal cracks to occur in the succeeding rolling process, and may result in the breaking of the bar during the cold process (drawing and rolling) following the rolling process.

Accordingly, it is necessary to detect the internal cavities in the casting bar on line in the continuous casting and rolling process thereby to control the continuous casting conditions and the quality of the casting bar itself.

Heretofore, a continuous on-line ultrasonic flaw detection method has not been employed in a continuous casting and rolling process.

In a conventional ultrasonic flaw detection method employing a water jet system or a water membrane gap system, the temperature of a material to be inspected is relatively high, and therefore a water evaporating area appears near the surface of the material to be inspected, which interrupts the transmission of the ultrasonic wave, as a result of which the detection cannot be carried out. This is a drawback accompanying the conventional ultrasonic flaw detection method.

SUMMARY OF THE INVENTION

Accordingly, an object of this invention is to overcome a difficulty concerning the acoustic mismatching between the limits at high temperature which is the most serious drawback accompanying the conventional ultrasonic wave flaw detection method employing the aforementioned water jet system or the like.

More specifically, an object of the invention is to provide a method of detecting the internal cavities in a continuous casting bar in which a pair of rollers, with hollow portions incorporating a probe for transmission and a probe for reception, respectively, are brought under pressure in contact with the casting bar to be inspected, thereby to make it possible to carry out ultrasonic flaw detection for the casting bar at high temperature which is 500°-600° C. if it is of aluminum and is 800°-900° C. if it is of copper, and an apparatus for practicing the method.

Another object of the invention is to detect, in a continuous casting and rolling process, the hollow defects in a casting bar with high accuracy before rolling, thereby to prevent troubles which may be caused in the following processes.

A further object of this invention resides in that in a continuous casting process, the internal cavities in a casting bar are detected, and the casting conditions are corrected according to the detection of the internal cavities to prevent the occurrence of internal cavities, thereby to greatly contribute to the control in quality of continuous casting bars.

The foregoing objects and further objects of the invention have been achieved by providing a method of detecting the internal cavities in a continuous casting bar in which two opposite surfaces of a casting bar delivered from a continuous casting machine are held between a pair of rollers each having a hollow portion and are pressurized at predetermined pressure thereby, and an amount of transmission of an ultrasonic wave having a predetermined frequency passing through the casting bar is detected by means of an ultrasonic wave device for transmission and an ultrasonic wave device for reception which are provided respectively in the hollow portions of the rollers to allow the ultrasonic wave to pass through the casting bar running through the rollers, thereby to detect the internal cavities in the casting bar, and an apparatus for practicing the method.

The nature, principle and utility of this invention will become more apparent from the following detailed description and the appended claims when read in conjunction with the accompanying drawings, in which like parts are designated by like reference numerals or characters.

DETAILED DESCRIPTION OF THE INVENTION

Figure 1:
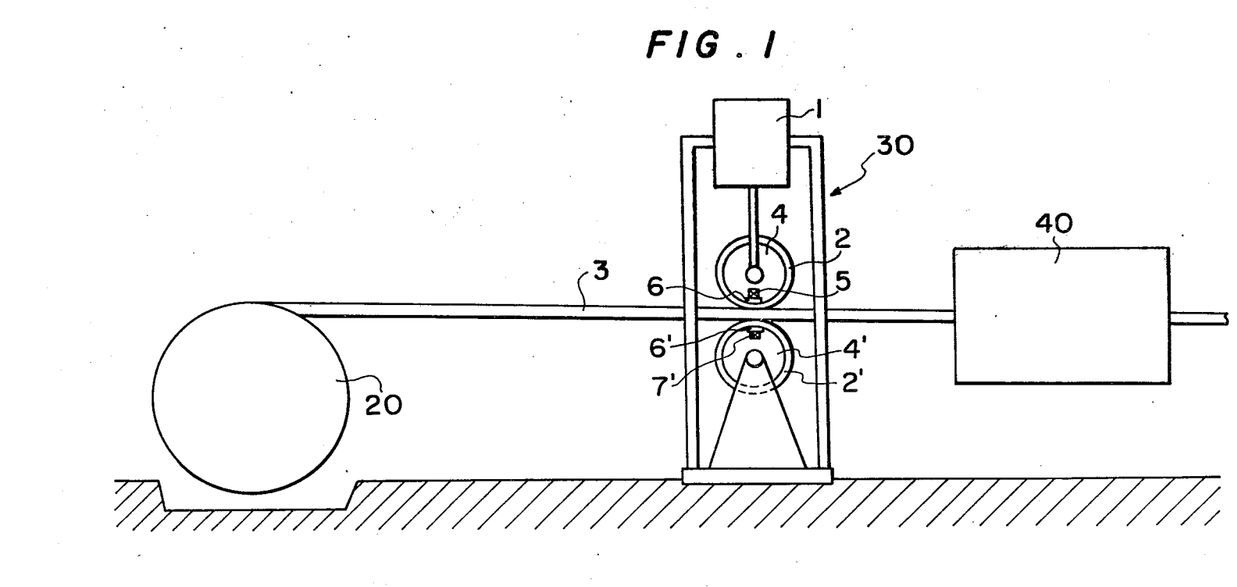
FIG. 1 is a side view illustrating relationships between an ultrasonic flaw detecting apparatus according to this invention, a casting machine and a rolling mill.
Figure 2:
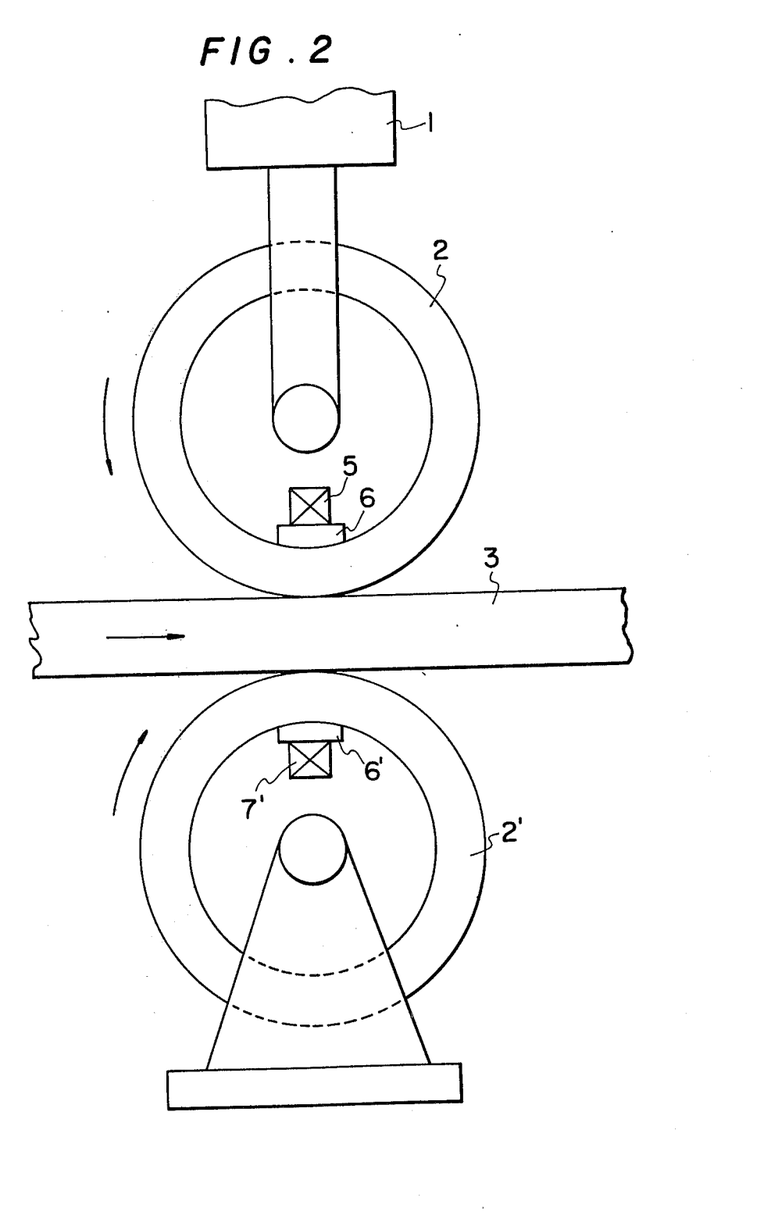
FIG. 2 is an enlarged side view illustrating essential elements of the ultrasonic flaw detecting apparatus according to the invention.

An ultrasonic flaw detecting method according to this invention is of a so-called opposite roller system in which, as shown in FIGS. 1 and 2, a casting bar 3 is supplied by a continuous casting machine 20 to a flaw detection station 30 and then to a rolling mill 40. In the flaw detection station, the casting bar is interposed between rollers 2 and is depressed with a pressurizing force great enough to allow an ultrasonic wave to be transmitted into the casting bar 3 by means of a pressurizing device 1.

In this invention, a pulse transmission method is employed as the ultrasonic flaw detecting method. An ultrasonic wave generated by a vibrator 5 for transmission built in a hollow portion of the roller 2 propagates into a shoe 6, the roller 2, the casting bar 3, the roller 2' and a shoe 6', and is received by a vibrator 7 for reception provided so as to confront the vibrator 5 for transmission. The rollers 2 and 2' are made of heat-resisting metal such as steel or heat-resisting steel. The shoes 6 and 6' are made of heat-resisting resin. The shoes 6 and 6' are fixedly secured in the respective hollow portions of the rollers, but are slid along the respective inner walls of the rollers through cooling oil which is circulated by an external oil circulating device (not shown). However, this method suffers from the following drawbacks, for instance:

(1) When the roller pressurizing power P is too small, the contact sections between the rollers 2 and 2' and the casting bar 3 are affected by the surface condition and shape of the material, or bar, to be examined, and therefore acoustic coupling therebetween can not be obtained.

(2) The surface condition of the continuous casting bar is poor; that is, a casting streak pattern is observed on the surface of the bar. Because of the surface streaky defects, the acoustic coupling is liable to be nonuniform, which affects the penetration of acoustic waves into the casting bar 3.

(3) In order to overcome the difficulties described in paragraphs (1) and (2), a great pressurizing power P is required.

In the detecting method according to this invention, the amount of transmission of an ultrasonic wave is increased by the pressurizing power P, and yet it is possible to reduce variation in the amount of penetration. In the detecting method according to the invention, if the pressurizing power P is made to be higher than 500 kg/cm$^2$, and 150 kg/cm$^2$ respectively for casting copper bars in hot state and casting aluminum bars, then the variation in the amount of transmission of an ultrasonic wave can be maintained less than 2 dB.

It has been known that the amount of attenuation of an ultrasonic wave for a casting bar in hot state is larger than that of a casting bar which is at room temperature. In the detecting method according to this invention, a flaw detecting frequency of 1 MHz was employed for casting copper bars, while a flaw detecting frequency of 1 MHz to 2 MHz was employed for casting aluminum bars, whereby the internal cavities (blowholes or pipe-shaped defects) in the casting bars in a hot state could be detected in the on-line system according to the method illustrated in FIG. 1.

In the method shown in FIG. 1, by abutting the roller 2 against the casting bar 3 with a predetermined pressure, the acoustical coupling between the rollers 2 and 2' and the casting bar 3 is improved, as a result of which the amount of transmission of the ultrasonic wave is increased. However, this method is still disadvantageous in that the variation in the amount of transmission of the ultrasonic wave is increased because of the surface roughness of the casting bar 3.

Figure 3:
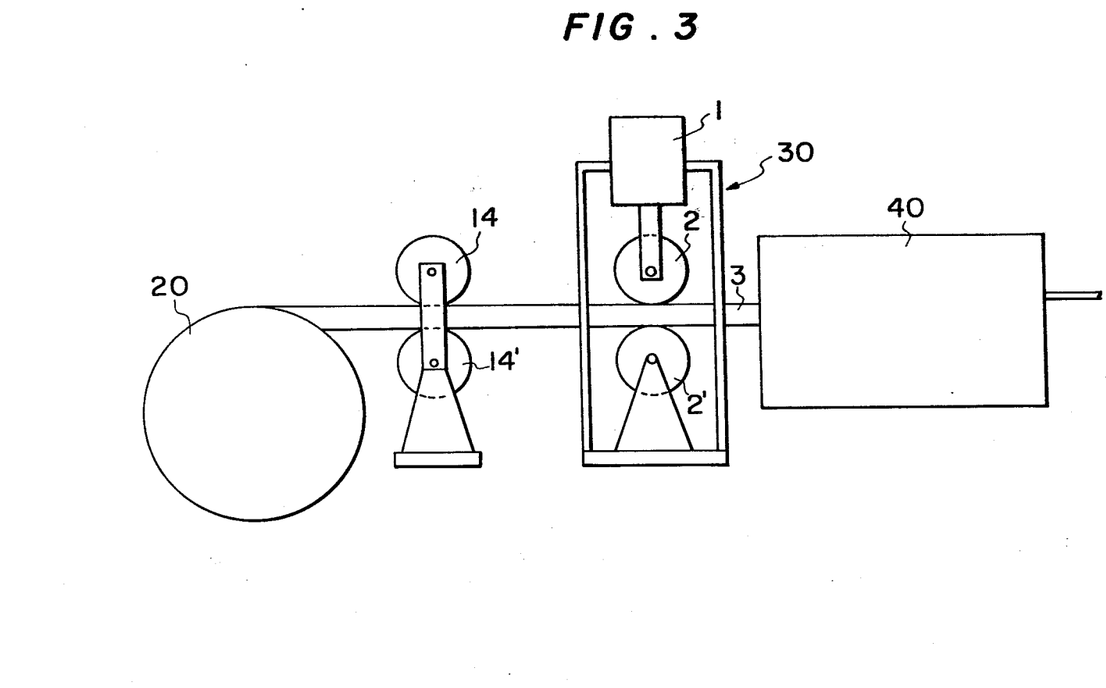
FIGS. 3 and 4 are explanatory diagrams for a description of other examples of the ultrasonic flaw detecting apparatus according to the invention.

In order to overcome the above-described difficulties, a method of increasing the pressurizing power P may be employed. However, if the pressurizing power is increased, then the material 3 to be inspected may be deformed, which adversely affects the rolling process. Therefore, shaping rolls 14 and 14', as shown in FIG. 3, for smoothing the surface condition of the casting bar 3 may be provided in front of the detecting device so as to decrease the variation in the amount of transmission of the ultrasonic wave.

Figures 4, 5:
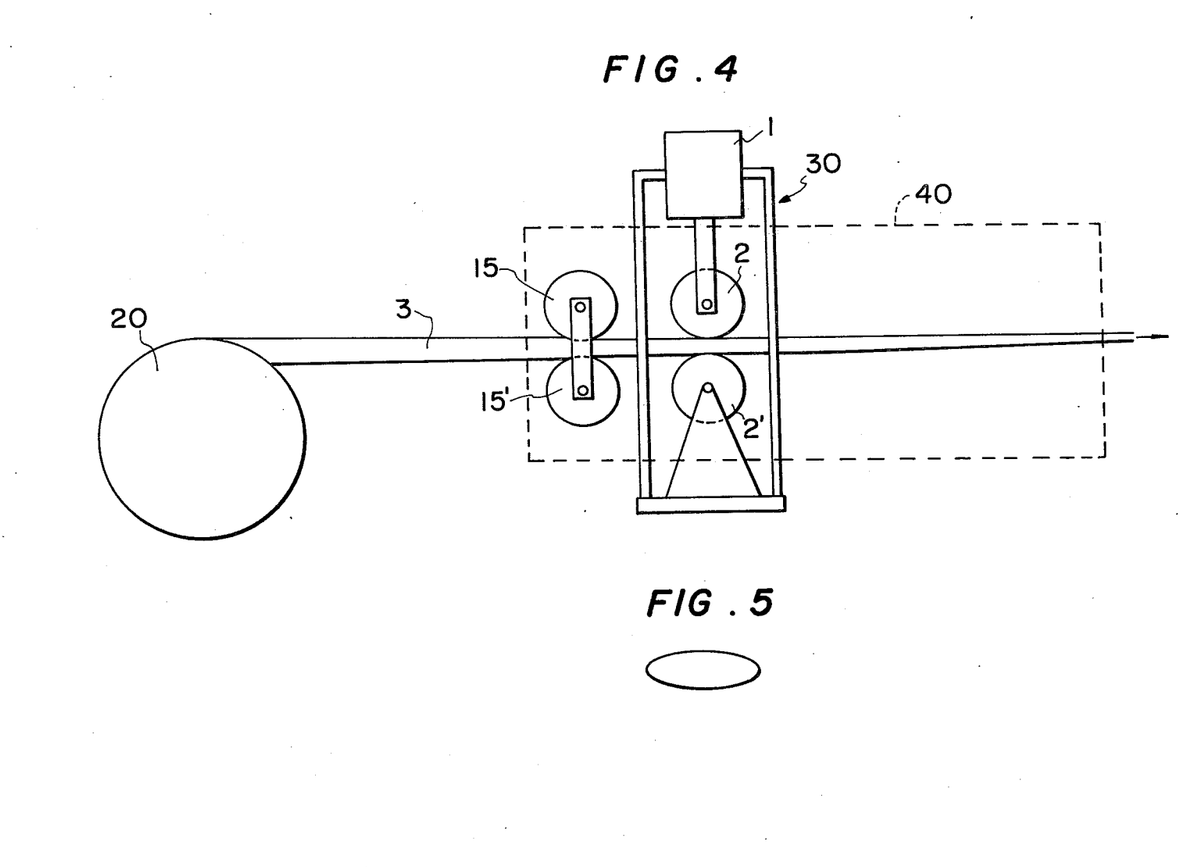
FIG. 5 is a sectional view of a material to be inspected in one embodiment of this invention.

For the same purpose, if the casting bar 3 is subjected to rolling, or it is allowed to pass through a rolling machine 15 instead of the rolls 14 and 14' as shown in FIG. 4, the surface of the casting bar 3 is smoothed. Therefore, the cavities in the casting bar 3 can be detected by the detecting device at the rear stage of the rolling machine with higher accuracy.

The foregoing is a fundamental description of the detecting method according to this invention in which ordinary rollers are employed as a pair of rollers 2 and 2' between which the casting bar 3 is held and pressurized. However, this method suffers from the following drawback in practice:

In the method the rollers are employed as a medium to transmit the ultrasonic wave into the casting bar. However, if the pressure applied to the rollers is small, the transmission of the ultrasonic wave at the interfaces between the rollers and the casting bar is insufficient, that is, the signal to noise ratio (S/N ratio) is low. Accordingly, in order to increase the signal to noise ratio, it is necessary to increase the pressure applied to the casting bar by the rollers. It is true that the transmission of the ultrasonic wave is improved by increasing the pressure; however, in this case meandering of the casting bar and blocking of a smooth flow of casting bar occur as secondary phenomena, which will exert a fatal beneful influence on the continuous casting.

Accordingly, in order to overcome the above-described difficulties, it is preferable to employ a modified method as described below.

Employed in this modified method are a pair of rollers, one of which is a roller for transmission whose outer wall is of a crown-shaped protruded surface, and the other of which is a roller for reception whose outer wall is of a planar surface.

Figure 6:
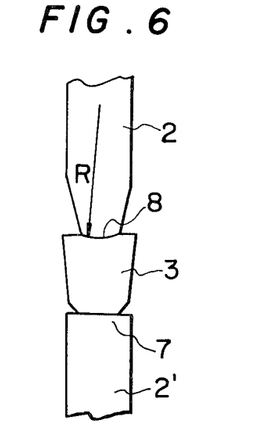
FIG. 6 is a sectional view illustrating the construction of rollers employed in another embodiment of a method according to this invention, and a state of contact between rollers and a casting bar.

FIG. 6 is a sectional view illustrating the structures of the rollers and a state of contact between the rollers and a continuous casting bar according to this modified method. The modified method is carried out similarly as in the case of FIG. 1, by utilizing the rollers shown in FIG. 6.

If a roller whose outer wall is of a planar surface is employed as the roller 2 for transmission as in the above-described case, it is necessary to apply a great load to depress the whole surface of the casting bar 3. However, if a roller 2 whose outer wall 8 is of a crown-shaped protruded surface is employed, then the casting bar 3 is depressed only at the central area of the upper surface thereof, and therefore the surface pressure of the roller can be improved with the same load; that is, the total load can be reduced. Furthermore, defects such as blowholes are, in general, provided in the central portion of a casting bar, and therefore the detection can be satisfactorily achieved by transmitting the ultrasonic wave into only the central portion of the casting bar. Thus, according to the modified method, the total load of the pressurizing rollers for obtaining a satisfactory interface condition can be reduced. As a result, braking action to the casting bar is minimized, and therefore the occurrence of meandering of the casting bar and an unsmooth flow of the casting bar are prevented, and in addition the transmission of the ultrasonic wave for detecting flaws is effectively carried out, and therefore the noise level can be considerably lowered.

In the modified method, the above-described effects can be obtained by allowing the shape of the outer wall 8 of the roller 2 for transmission to be of an arc-shaped or elliptic-arc-shaped protruded surface. The radius of curvature R thereof is suitably selected according to the sectional dimension of a casting bar; and is not limited to any particular value. For instance, in the case of a trapezoidal-shaped casting bar which has a sectional area 3600 mm², about 75 mm in upper surface width and about 62 mm in height, the radius of curvature thereof is of the order of approximately 1000 mm.

The width of the outer wall of the roller 2 for transmission is suitably determined from the sectional dimension of a casting bar, the size of the vibrator for transmission and that of the vibrator for reception. Normally, the width of the outer wall of the roller 2 for transmission is approximately 30 to 60 mm. In the case where the width of the outer wall of the roller 2 for transmission is less than 30 mm, it is insufficient for the width of the ultrasonic wave, and therefore the amount of transmission of the ultrasonic wave is decreased. On the other hand, in the case where the width of the outer wall of the roller 2 for transmission is larger than 60 mm, the pressure for depressing the casting bar is excessively increased.

The width of the outer wall of the roller 2' for reception is preferably larger than the lower surface width of a casting bar, and it is not limited.

No limitation is provided for the diameter of the vibrator for transmission and that of the vibrator for reception; however, approximately 15-20 mm and 20-25 mm are suitable diameters for the vibrator for transmission and the vibrator for reception in practice, respectively.

Furthermore, in the method according to this invention, better effects can be obtained by employing the following method with respect to the transmission of an ultrasonic wave.

Figure 7:
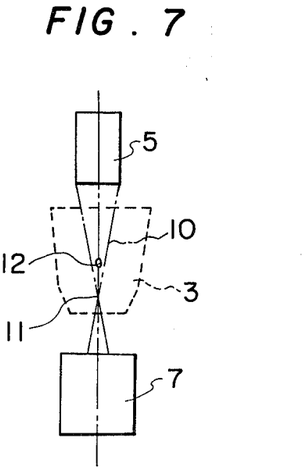
FIG. 7 and FIG. 8 are sectional views for a description of specific embodiments of this invention.

One of the methods will be described. Since internal defects such as blowholes are liable to be caused in the central portion of a casting bar 3, as is shown in FIG. 7 a lens-coupled vibrator is employed as the vibrator 5 for transmission in such a manner that the acoustic wave beams 10 emitted from the vibrator 5 for transmission toward the vibrator 7 for reception are focused (11) below the central portion of the casting bar where defects are liable to be caused. When the ultrasonic wave is transmitted in this manner, the acoustic wave is applied collectively to the internal defects in the casting bar, as a result of which the S/N ratio is increased.

Figure 8:
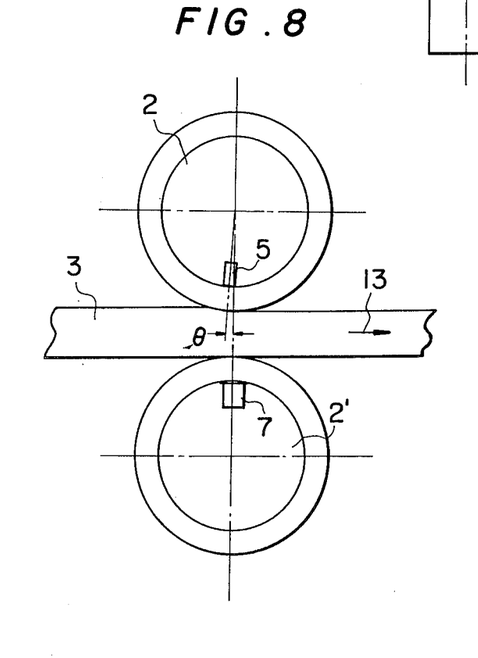

In another method, as is shown in FIG. 8, the vibrator 5 for transmission is inclined through about 1-2 degrees with respect to the line connecting the vibrator 5 for transmission and the vibrator 7 for reception, in a direction opposite to the advancing direction 13 of the casting bar 3. It has been confirmed through experiment that in this method the S/N ratio is improved.

Now, various examples of this invention will be described:

EXAMPLE 1

Employed as a casting bar was a copper casting bar whose sectional shape was elliptical as shown in FIG. 5, and whose temperature was approximately 900° C. Under the following conditions, ultrasonic flaw detection was carried out with the device as shown in FIG. 3:

The radii of the shaping rolls 14 and 14'—200 mm
The radii of the rollers 2 and 2—300 mm
The pressurizing power P by the roller 2—Total load 3.6 tons (corresponding to a pressure of 500 kg/cm²)
The running speed of the casting bar 3—15 m/min
The ultrasonic wave frequency—1 MHz Upon investigation for correspondence relationships between the defects and the flaw detection results obtained by recording the amplitudes of signals received by the vibrator 7 for reception with respect to the casting bar having the sectional shape as shown in FIG. 5, blowholes approximately 4.5 mm$\phi$×30 mm, 4 mm$\phi$×29 mm and 3.5 mm$\phi$×27 mm (where $\phi$ designates a diameter) were confirmed from defect signals No. 1, No. 2 and No. 3 in flaw detection. This reveals that the ultrasonic flaw detection was stable. The flaw detection in this example was carried out after the continuous casting bar, as shown in FIG. 3, had been rolled by the rolls 14 and 14 to smooth the surface thereof.

EXAMPLE 2

Figure 9:
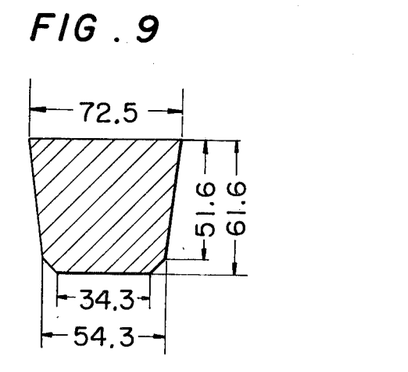
FIG. 9 is a diagram showing the sectional dimensions of a continuous casting bar in an embodiment of this invention.

An aluminum casting bar for electrical use (hereinafter referred to as "an EC grade aluminum casting bar" when applicable) having sectional dimensions as shown in FIG. 9 was casted at a rate of 21 cm/sec by a continuous casting machine. The internal defects were continuously detected by using the detecting device before the casting bar was loaded in the rolling machine as shown in FIG. 1.

The detection was carried out under two different conditions as indicated in Table 1 below:

Table 1

|  | No. 1 | No. 2 |
|---|---|---|
| Roller's pressurizing load | 2.0 tons (corresponding to 300 kg/cm²) | 1.0 tons (corresponding to 150 kg/cm²) |
| Upper roller (section) | Planar surface, width 70 mm | Curvature 1000 mm, width 50 mm |
| Lower roller (section) | Planar surface width 100 mm | planar surface width 100 mm |
| Vibrator for transmission | 25 mm$\phi$ vertical type | 15 mm$\phi$ lens-coupled type |
| Vibrator for reception | 25 mm$\phi$ | 20 mm$\phi$ |
| Ultrasonic wave frequency | 1.0 MHz | 1.0 MHz |

Figure 10A:
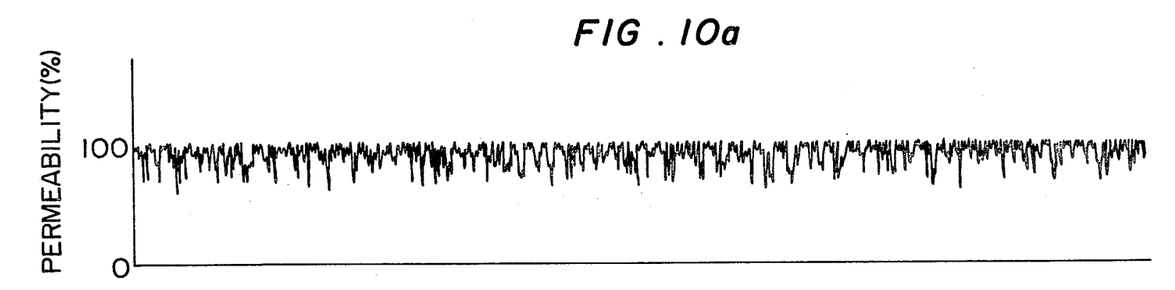
FIG. 10a is a chart indicating the amount of transmission of an ultrasonic wave observed when the method according to this invention is applied to a casting bar shown in FIG. 9, and FIG. 10b that observed when a conventional method is applied to the same casting bar.
Figure 10B:
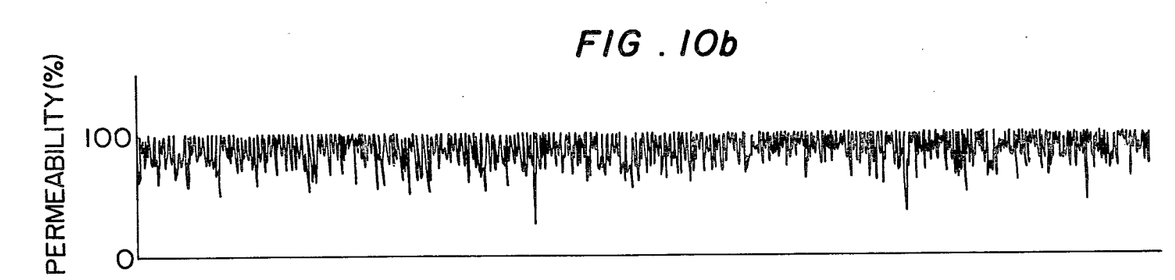

The chart (the chart speed being 1 mm/sec) for the amount of transmission of the ultrasonic wave was as indicated in FIG. 10.

As is apparent from the comparison between the case (No. 1) of FIG. 10b where the upper roller whose outer wall of a planar surface was employed and the case (No. 2) of FIG. 10a where the upper roller whose outer wall was of a crown-shaped protruded surface, noises are greater and defects are unclear in the case (No. 1), while noises are small and defects are clear in the case (No. 1). That is, it is obvious from FIG. 10 that the internal defects can be detected with higher accuracy and higher sensitivity according to the method No. 2.

As is apparent from the above description, in this invention, two opposite surfaces of a casting bar are held between a pair of rollers each having a hollow portion and are pressurized at a predetermined pressure therewith, and an ultrasonic wave is effectively transmitted into the casting bar through the rollers by means of ultrasonic wave devices for transmission and reception which are built in the rollers, respectively. Therefore, the cavities in the casting bar in hot state can be detected with high accuracy in the continuous casting process, as a result of which troubles which otherwise may be caused in the succeeding processes can be prevented. Furthermore, as the casting conditions are corrected, the occurrence of cavities such as blowholes can be suppressed. Thus, the invention can greatly contribute to the control in quality of the casting bar during the continuous casting process.

In addition, in the case where a roller whose outer wall is of a crown-shaped protruded surface is employed as the upper roller for transmission according to the invention, the state of contact between the roller and the casting bar can be maintained satisfactory even with a smaller pressure. As a result, it is possible to prevent the casting bar from meandering and from flowing unsmoothly. In addition, the noise level affecting the abutting interface conditions is suppressed, which leads to an improvement of the S/N ratio and to detection of the internal defects in the casting bar with higher accuracy and higher sensitivity.

What is claimed is:

1. A method of detecting the internal cavities in a continuous casting bar, comprising:
   holding between first and second rollers with a predetermined holding pressure, two opposite surfaces of a casting bar delivered from a continuous casting machine, each said roller having a hollow portion;
   transmitting through said casting bar, through a crown-shaped outer wall of said first roller in contact with said casting bar, an ultrasonic wave having a predetermined frequency generated by an ultrasonic wave device for transmission disposed within the hollow portion in said first roller; and
   detecting, by means of an ultrasonic wave device for reception disposed within the hollow portion of said second roller, the amount of said ultrasonic wave which is transmitted through said casting bar and through a planar surface of the outer wall of said second roller in contact with said casting bar.

2. A method as claimed in claim 1, in which a vibrator in said ultrasonic wave device for transmission is of a lens-coupled type, and acoustical wave beams emitted from said vibrator toward a vibrator in said ultrasonic wave device for reception are focused at a position which is closer to said vibrator in said ultrasonic wave device for reception than the central portion of said casting bar where internal cavities are liable to be formed.

3. A method as claimed in claim 1, in which said vibrator in said ultrasonic wave device for transmission is inclined through one to two degrees with respect to a phantom line connecting said vibrator in said ultrasonic vibrator for transmission and said vibrator in said ultrasonic vibrator for reception, in a direction opposite to the advancing direction of said casting bar.

4. An apparatus for detecting internal cavities in a continuous casting bar, which comprises: a pair of rollers for holding and pressurizing two opposite surfaces of a casting bar delivered from a continuous casting machine, each roller having a hollow portion and being rotatable around a respective shaft; a pressurizing device coupled to at least one roller of said pair of rollers, for depressing said roller toward the upper surface of said casting bar; an ultrasonic wave probe for transmission disposed within the hollow portions of one of said rollers having a crown-shaped outer wall and an ultrasonic wave probe for reception disposed within the hollow portion of the other of said rollers having a planar outer wall and supported so as to be maintained at predetermined positions without following the rotations of said rollers, respectively; and shoes provided respectively in said hollow portion of said rollers, each shoe being interposed between an inner wall, forming the respective hollow portion, of the respective roller and the respective ultrasonic wave probe, said ultrasonic wave probes being opposed to each other through said casting bar so that an ultrasonic wave is transmitted through said casting bar.

* * * * *